United States Patent [19]

Hill et al.

[11] 4,320,195

[45] Mar. 16, 1982

[54] STEROID PRODUCTION

[75] Inventors: Frank Hill, Mettmann-Obschwarzbach; Wolfgang Preuss, Monheim; Joachim Schindler, Hilden; Rolf Schmid, Dusseldorf; Alfred Struve, Hilden, all of Fed. Rep. of Germany

[73] Assignee: Henkel Kommanditgesellschaft auf Aktien, Duesseldorf, Fed. Rep. of Germany

[21] Appl. No.: 29,415

[22] Filed: Apr. 12, 1979

[30] Foreign Application Priority Data

Apr. 17, 1978 [AT] Austria ............................... 2662/78

[51] Int. Cl.³ ..................... C12P 33/16; C12N 15/00; C12N 1/20; C12R 1/15
[52] U.S. Cl. ........................................ 435/55; 435/52; 435/54; 435/56; 435/172; 435/253; 435/843

[58] Field of Search .................. 435/55, 172, 253, 54, 435/52, 56, 843

[56] References Cited

U.S. PATENT DOCUMENTS 4,029,549  6/1977  Antosz et al. ......................... 435/55
4,214,052  7/1980  Woucha et al. ....................... 435/55

FOREIGN PATENT DOCUMENTS 2408621  7/1979  France ................................. 435/55

*Primary Examiner*—Thomas Wiseman
*Attorney, Agent, or Firm*—Forrest L. Collins; Patrick J. Span

[57] ABSTRACT

A process for the production of useful steroids obtained by side chain degradation of sterol source materials through the use of microorganisms is described.

17 Claims, No Drawings

STEROID PRODUCTION

BACKGROUND OF THE INVENTION

The first report on microbial conversion of steroid compounds was published as early as in 1937 when Mamoli and Vercellone (Ber. 70, 470 and Ber. 70, 2079) described the stereospecific reduction of 17-ketosteroids to 17-β-hydroxysteroids. In 1952, Peterson and Murray (U.S. Pat. No. 2,602,769) described a commercially important process for the 11-α-hydroxylation of progesterone by *Rhizopus nigricans.*

Since that time, a great variety of conversions of steroid compounds by means of microorganisms have been described (see, for ex. W. Charney and H. L. Herzog, Microbial Transformation of Steroids, Academic Press, New York, 1967).

Despite this great number of proposals for the microbial transformation of steroid compounds, only a few of these reactions are suitable for the production of important steroid hormones from starting materials which are readily accessible and available in large amounts. In this connection, the sterol compounds contained in 17-C-alkyl side chains of plant or animal origin are to be mentioned primarily, for example, sterols of the cholestane, campestane and stigmastane series.

It has been known that a great variety of microorganism strains, e.g. those of Achromobacter, Arthrobacter, Bacillus, Brevibacterium, Corynebacterium, Flavobacterium, Microbacterium, Micybaterium, Nocardia, Protaminobacter, Serratia and Streptomyces are capable of growing on sterol compounds of the kind mentioned, e.g. on cholesterol, as the carbon source (see for ex. Arima et al, 1969, Agr. Biol. Chem. 33: 1636–1643). In doing so, both the ring system and any side chains, which may be present on the ring system are attacked as a rule in a non-specific manner by the microorganisms or degraded in their growth, the attack and degradation in the ring system being predominantly the preferred and/or faster reaction. A recently published paper by Arima et al, Agric. Biol. Chem. 42(2), 411–416 reports on work for the transformation of cholesterol by microbial side chain degradation in the presence of inhibitors to inhibit the ring degradation in the steroid structure.

According to this publication, a considerable proportion of the about 200 wild strains having been tested was capable under the influence of the inhibitors to lead to largely selective side chain degradation in C-17 of the starting material. Some of the strains lead to 3-oxopregna-1,4-diene-20-carboxylic acid (Δ-1,4 BNC) in varying yields.

Japanese Pat. No. 152800 Arima, relates to 3-oxobisnorchola-1,4-dienic acid as being useful as a raw material for preparing hormonal steroids. It is prepared by culturing a microorganism capable of converting sterols or their derivatives with dehydrogenation A ring *Nocardia cholarina* IFO 3338, *N. erythropolis* NI 9110 FERM-P 3315, *Mycobacterium abium* IFO 3082, *Protaminobacter alboflavus* IAM 1040, *Bacillus roseus* IAM 1257. Typical microorganisms are *Mycrobacterium lacticum* IAM 1640 FERM-P 3317, *Serratia marcescens* IAM 1225 FERM-P 3316 etc. The medium contains sterol (e.g. cholesterol, beta-sitosterol, gamma-sitosterol, campesterol, ergosterol, stigmasterol etc.), or an A-ring dehydrogenated derivative (e.g. 4-en-3-one compounds, 1,4-dien-3-one compounds etc.). It also contains a chelating agent capable of forming a complex salt with iron or copper (e.g. 1-nitroso-2-naphtol, salicylaldoxime, chromotoropic acid, alpha,alpha'-dipyridyl, 8-oxyquinoline, nitroso.phenylhydroxylamine, 1-nitroso-2-naphtol-3,6-disulphonic acid, o-phenthroline, tetrahydroxyanthraquinone, ethylenediaminetetraacetic acid, et.) or a nickel or cobalt ion.

The starting sterol or a dehydrogenated derivative is added to the medium in the form of fine powders or solutions in solvents or suspensions in water.

East German Pat. No. 195528 relates to the production of 20-carboxy-1,4-pregnadien-3-one (I) carried out by treating sterols and their 3-substituted derivatives with sterol-degrading microbial cultures under controlled fermentation conditions in the presence of inhibitors for suppressing cleavage of the steroid ring structure.

Due to the potential importance of natural sterol compounds having 17-C side chain or plant original (phytosterols) or animal origin (cholesterol) as starting material for high quality pharmaceutic compositions having steroid basic structure, a great number of attempts have been made to achieve selective side chain degradation on the microbiological route. A summarizing review of these works is found in Adv. Appl. Microbiol. 22, 29 (1977) 29–58, Christoph K. A. Martin "Microbial Cleavage of sterol Side Chains". Reference is made especially to Chapter IV of this publication which classifies the three methods used heretofore for the selective side chain cleavage under A to C. Accordingly, the prior art proposals fall within the following three groups: Transformation of the ring structure of the sterol starting compound in such a manner that the mechanism of ring cleavage is prevented so that the selective side chain cleavage becomes possible; concomitant use of inhibitors to inhibit the steroid ring degradation and or the growth of the microorganism, and, finally the search for microorganism mutants which lead to the desired, as extensive a selective side chain degradation as is possible.

According to said process of prior art, the final products obtained predominantly of the microbial degradation are 17-ketosteroid compound which, while valuable as intermediates for the technical production of hormones of the estrane-androstane- and spirostane-series, are less suitable for the preparation of steroid hormones of the pregnane series, e.g. progesteron, hydrocortison, cortison, prednison, prednisolon, triamcinolon and the like. In the latter cases, it is necessary to incorporate again chemically in 17-position stereospecific side chains.

Heretofore, it was possible only occasionally to obtain as metabolism products of microbial degradation steroid compounds which contain an alkyl side chain group and especially the residue of α-propionic acid in 17-C position. Steroid compounds of this type would be useful especially for the commercial-scale production of steroid hormones of the pregnane series from sterols of natural origin. It is evident in this connection that the recovery of partial sterol degradation products of this kind is particularly difficult because this requires not only the selective side chain cleavage with simultaneous prevention of breaking-up and degradation of the ring structure, but additionally the growth of the microorganisms with cleavage of the side chains must be ceased in a stage which, according to knowledge gained so far, is merely a transitory station until the 17-ketosteroid structure has been reached. J. M. Whitmarsh describes in The Biochemical Journal, 90, 1964, 23 p to 24 p, the microbiological degradation of cholesterol with a nocardia culture in the presence of inhibitors such as 8-hydroxyquinoline with formation of small amounts of 3-oxo-pregna-4-ene-20-carboxylic acid (Δ4 BNC) and 3-oxo-pregna-1,4-diene-20-carboxylic acid (Δ1,4 BNC). The recently published U.S. Pat. No. 4,029,549 (Antosz et al) describes the microorganism mutant NRRL B-8119 which is said to permit the selective degradation of 17-C steroid compounds having 8 to 10 carbon atoms in the 17-C alkyl group to form 9α-OH AD and 9α-OH BN acid. However, as is shown especially by chapter IV C of the publication by C. K. A. Martin, loc.cit., pp. 50 to 52, there exists up to-date no reliable method for the microbiological production of 17-C-steroid-α-propionic acid compounds from 17-C-side chain steroid substrates or for the reproducible recovery of microorganism defective block mutants which are capable of furnishing 17-C steroid-α-propionic acid compounds in a reliable manner and in high yields as the end product of enzymatic degradation even if the process is to be operated in the absence of inhibitors of the kind mentioned. However, operation in the absence or in the presence of only small amounts of the inhibitors must appear to be desirable for technical reasons, e.g. because of the desired high space-time yields.

It is an object of the invention to permit the production of 17-C-steroid-α-propionic acid compounds in commercially useful and improved yields by selective microbial degradation of 17-C-side chain steroid substrata. This is to be achieved with the use of defective block mutant microorganisms which have been prepared and selected in a directive manner and previously recovered from suitable wild strains. In particular, it should be possible but by no means mandatory in this process to use the selected defective block mutants also in the absence of inhibitors which inhibit the steroid ring degradation and/or the growth of microorganisms. Another object of the invention is the safe and reproducible production of the defective block mutant microorganisms which are suitable for the improved, in particular inhibitor-free commercial recovery of 17-C-steroid-α-propionic acid compounds from sterols of natural origin.

In a narrower sense, a particular object of the invention is the microbial production of 3-oxo-pregna-4-ene-20-carboxylic acid (Δ4 BNC) and/or 3-oxo-pregna-1,4-diene-20-carboxylic acid (Δ1,4 BNC) by the method described herein. The starting material for the microbiological production of these compounds should be in particular natural and/or vegetable sterols which, as waste products, have hardly gained any practical importance up to the present. Simple derivatives of these natural starting materials are also contemplated as suitable starting materials for the invention.

In a particular embodiment, it is an object of the invention to provide methods of producing highly active defective block mutant microorganisms for the particular sterol starting material used in each given commercial-scale process thereby permitting the adaptation of the sterol starting material and the defective block mutant microorganism to be selected. The products of the process according to the invention Δ-4 BNC and Δ1,4 BNC are valuable intermediate products for the production, for ex., of compounds of the progesterone series.

SUMMARY OF THE INVENTION

Accordingly, in a first embodiment, the invention relates to a process for the production of 17-C-steroid-α-propionic acid compounds by enzymatic side chain degradation on 17-C-side chain steroid substrata, the process being characterized in that (a) defect block mutant microorganism products which also yield in the absence of inhibitors inhibiting the steroid ring degradation and/or the growth of the microorganisms, steroid compounds having the 17-C-propionic acid residue, are cultivated in an aqueous culture medium under aerobic conditions in the presence of the steroid substratum with accumulation of the 17-C-steroid-α-propionic acid compounds in the fermentation broth and (b) the formed 17-C-steroid-α-propionic acid compounds are isolated.

A particular object of the invention is a process for producing 3-oxo-pregna-4-ene-20-carboxylic acid (Δ-4 BNC) and/or 3-oxo-pregna-1,4-diene-20-carboxylic acid (Δ-1,4 BNC) by microbial side chain degradation on 17-C-side chain steroid substrates, characterized in that (a) a microorganism producing Δ-4 BNC and/or Δ-1,4 BNC also in the absence of inhibitors for inhibiting the steroid ring degradation and/or the growth of microorganisms is cultivated in an aqueous culture medium under aerobic conditions and in the presence of a 17-C-side chain steroid substratum with accumulation of 3-oxo-pregna-4-ene-20-carboxylic acid and/or 3-oxo-pregna-1,4-diene-20 carboxylic acid (b) and, thereafter, the 3-oxo-pregna-4-ene-20-carboxylic acid and/or 3-oxo-pregna-1,4-diene-20-carboxylic acid formed is isolated. The yield of Δ-4 BNC and/or Δ-1,4 BNC shall be preferably at least 15% by weight, based on the used steroid substratum.

The structural formulae of the stated compounds Δ-4 BNC and Δ-1,4 BNC are the following:

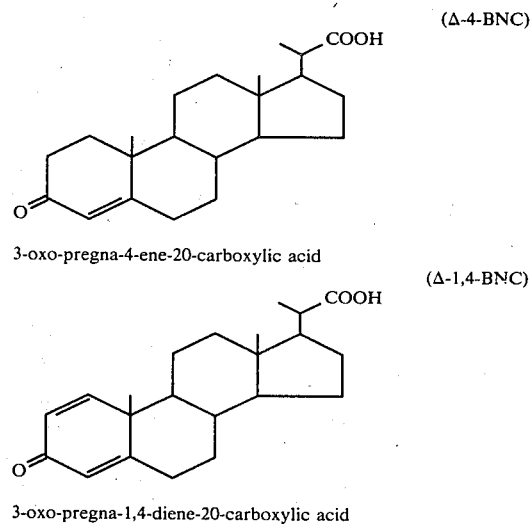

3-oxo-pregna-4-ene-20-carboxylic acid (Δ-4-BNC)

3-oxo-pregna-1,4-diene-20-carboxylic acid (Δ-1,4-BNC)

In a further embodiment, the invention relates to a process for the production of aerobically growing defective block mutants of microorganisms which are capable of the commercial-scale production of 17-C-steroid-α-propionic acid compounds, especially of the production of 3-oxo-pregna-4-ene-20 carboxylic acid and/or 3-oxo-pregna-1,4-diene-20 carboxylic acid from 17-C-side chain steroid substrata, e.g. from sterol compounds of animal or plant origin, by at least largely selective side chain degradation, if desired, in the absence of inhibitors inhibiting the steroid ring degradation or the growth of the microorganism, the process being characterized by (1) isolating and cultivating a microorganism wild strain capable of aerobic growth on sterol compounds as the sole carbon source while giving preference to 17-C-side chain degradation over ring degradation, (2) subjecting the wild strain to a mutation treatment known per se;

(3) cultivating the mutant population on a separating medium (accumulation medium for the mutants desired) on which the mutants producing 17-C-steroid-α-propionic acid compounds do not or substantially do not grow while the undesirable accompanying mutant strains grow and are killed off thereby or during their growth, and (b) cultivating the remaining fraction of the mutant strains on 17-C side chain sterol compounds while isolating the strains having optimum production of the 17-C-steroid-α-propionic acid compounds.

The invention further comprises the defective block mutants produced by this process, especially those producing Δ-4 BNC and/or Δ-1,4 BNC. In this connection, the invention relates especially to a new block mutant Chol.spec. 73-Mll which was deposited with the Centraalbureau voor Schimmel-cultures, Baarn, the Netherlands, under No. CBS 437.77 and with the American Type Culture Collection, Rockville, Md., USA, under No. ATCC 31385. This new block mutant is suitable for the inhibitor-free preparation of 3-oxo-pregna-4-ene-20-carboxylic acid or 3-oxo-pregna-1,4-diene-20-carboxylic acid also in the absence of said inhibitors from sterols of natural or vegetable origin. It is recovered according to the process of the invention from the new wild strain Chol.spec. 73 also isolated for the first time by applicants and belonging to the object of the invention, it being deposited under No. CBS 660.77 with the Centraalbureau voor Schimmelcultures, Baarn, The Netherlands, and with the American Type Culture Collection, Rockville, Md., USA under No. ATCC 31384, said wild strain belonging to the group of coryneform bacteria.

DETAILED DESCRIPTION OF THE INVENTION

The Extraction of the Defective Block Mutants of Microorganisms according to the Invention A decisive object of the invention resides in the probably original provision of a safely reproducible process for obtaining defective block mutants of the disclosed type, i.e. of microorganisms which can be obtained by quite a specific combination of selections and mutations with another subsequent selection from wild strains, which may grow on the steroid compounds of the disclosed type. The defective block mutants of microorganisms obtained according to the process of the invention are characterized in that they are blocked to a far extent against a growth on the steroid ring structure, while consuming said rings as a carbon source, and, on the other hand, the microorganism mutants obtained according to the invention are also blocked so sufficiently against the degradation of an alpha-propionic acid residue present or formed in 17-C-position at the steroid, that the positive preparation of the 17-C-steroid-alphapropionic acid compounds from corresponding steroid substrata with long 17-C side chains and their isolation from the fermentation broth will be possible technically in good yields. It is particularly advantageous that, if desired, the process may be carried out in the absence of inhibitors of the type mentioned above; see, for example, Christoph K. A. Martin, loc. cit., Chapter IVB. This is rendered possible by the combination according to the invention of a specific selection of wild strains followed by mutation and selection steps.

In the process according to the invention for the recovery of the block mutants desired, the following four process steps are carried out in succession:

Stage 1: Directed selection of wild strains of microorganisms.

Stage 2: Mutation treatment.

Stage 3: Separation of the mutant population produced in stage 2 or enrichment of the desired mutants from the total mutant population recovered.

Stage 4: Cultivation of the mutant strains separated or enriched in stage 3 and selection of the block mutant strains with optimal production of the desired 17-C-steroid-alpha-propionic acid process product.

Said four steps of the process can be performed once in succession for the recovery of the desired defect block mutants. However, it can be useful in this process to repeat steps 2 or 3 once or several times in such a way that the desired mutant population separated—or enriched—in step 3 is subjected again to the mutation process of step 2 and then, in step 3, is separated again. Steps 1 to 4 mentioned above will now be described in greater detail.

Step 1: Isolation of suitable wild strains

The wild strains of micro-organisms to be selected should be able to grow on steroid compounds, in particular on steroid compounds with 17-C side chains under aerobic conditions. The strains which are suitable for the invention preferably possess at least approximately the same speed of degradation for the side chain as for the ring portion of the steroid compound. However, the wild strains preferably show an increased speed of side chain degradation, as compared with ring degradation.

The isolation of the wild strains may be effected in a known manner from soil samples. Due to the wide distribution of plant and animal sterol compounds, suitable wild strains of the kind mentioned are found substantially generally in soil samples of any origin. They are cultivated under aerobic conditions in the presence of an aqueous culture medium and preferably in the presence of a steroid compound having a 17-C-side chain as the sole carbon source. It is possible, but by no means necessary, to provide already at this point of the selection procedure according to the invention that type of steroid compound as carbon source which is finally intended to be degraded by the defective block mutants desired. If, for inst. cholesterol or a phytosterol is intended to be ultimately degraded to the 17-C-steroid-alpha-propionic acid compound, one of these natural sterol compounds, if desired, the specific sterol compound to be used in the commercial-scale process, may be present as the preferably sole carbon source in the otherwise conventional culture medium for the selection and cultivation of the wild strain. It has, however, been found that it is not necessary to effect at this point an adaptation between the sterol carbon source for the selection and cultivation of the wild strain and the sterol compound to be finally used in the steroid degradation process.

Within the overall procedure, the selection of the suitable wild strains is of a particular importance. It has been found that ordinarily the wild strains predominantly prefer ring degradation to a side chain degradation. The wild strains to be selected according to the invention should show at least about the same rate of degradation for the side chains as for the ring portion of the steroid compounds. However, it is particularly preferred to select and cultivate those wild strains which, when growing on sterol compounds with saturated or unsaturated alkyl groups in 17-C position, preferably groups having 8 to 10 C atoms, give a selective degradation performance—measured under the standard conditions described hereinafter—according to the general formula $$I = a \cdot 10^b$$

wherein a is the growth factor and b is the selectivity factor as defined hereafter.

The selectivity index I which is characteristic of the selection of the suitable and of the preferred wild strains is, therefore, obtained as the product of the growth factor a and the selectivity factor b according to the formula given above. The numerical value of I for the wild strains of the preferred micro-organism wild strains is at least 10. Higher numerical values for I are desirable and may, for example, be at least 100. When selecting wild strains from a larger isolated wild strain population, it may be desirable to subject the strains, having the highest values for I, to the further stages of the process according to the invention. Thus, it may be particularly advantageous to select wild strains for which the value of I is at least $10^5$. It has, moreover, been found, that the absolute value of I can be influenced by the choice of the particular steroid substrate to be used as carbon source. Thus, it is possible, for example, that a selected wild strain grows significantly better when cultivated on a sterol compound of animal origin in the first selection step discussed herein—and correspondingly produces a higher value for I—than on a vegetable sterol as carbon source. Regardless hereof, the previously given preferred conditions for the selection of the wild strains are applicable.

The determination of the growth factor a and the selectivity factor b of the wild strain growth is effected under the following standard conditions:

(aerobic processing):

Growth factor a:

The particular microorganism strain is incubated in 500 ml. Erlenmeyer flasks (100 ml. nutritive solution of the composition described below) at 30° C. on a shaking device (shaking cycles: 150 rpm).

The growth medium has the following composition (per liter):

1.0 g $KH_2PO_4$
0.5 g $MgSO_4 \cdot 7 H_2O$
0.1 g NaCl
0.1 g $CaCl_2 \cdot 2 H_2O$
5 g $(NH_4)_2 SO_4$
1.0 g Tween 80 (polyoxyethylene sorbitane monooleate)
2.0 g of the C-17 side chain sterol compound, e.g. cholesterol or sitosterol
0.5 g yeast extract
0.01 g l-histidine
0.02 g dl-methionine
0.02 g dl-tryptophane
2γ biotine
400γ calcium pantothenate
2γ folic acid
2000γ inositol
400γ niacin
200γ p-aminobenzoic acid
400γ pyridoxine hydrochloride
200γ riboflavin
400γ thiamine hydrochloride
trace element solution
pH value of the growth medium 6.8

For the measurement of growth (cell density) aliquote amounts of cell suspension are taken periodically from the agitated cultures, and the particular extinction (E') is measured against distilled water in a Zeiss photometer (type PL 4) at a wave length of 620 mn (layer thickness d = 1 cm). The initial extinction, before beginning of growth $E_0$ (i.e. at the time $t_0$) is about 0.775. The suspensions are diluted sufficiently that measurements can be made in the range $E' = 0.7$.

The growth factor a results as the maximim optical density of the cell suspension at the end of the logarithmic growth phase (time $T_1$, extinction $E_1$) which is reached in five days, at the latest, under the culture conditions given, i.e. $a = \Delta E = E_1 - E_0$.

Selectivity factor b:

The strains to be tested are cultivated in nutritive bouillon I (Merck) plus 0.1% Tween 80 (polyoxyethylene sorbitane monooleate) plus 0.1% sterol compound, e.g. cholesterol, for 48 hours at 30° C., and then the cells are washed with a buffer and resuspended in phosphate buffer (pH 7.5). The degradation of the sterol compound is measured in parallel amounts with a radioactively tagged sterol compound e.g. 4-14-C- and 26-14-C-cholesterol or the corresponding radiactively tagged sitosterol compounds in Warburg vessels.

To 2.4 ml cell suspension in the main container is added 0.2 ml sterol solution (e.g. Cholesterol solution) (5 μmol with about 0.1 μCi tagged substratum in 0.1% Tween 80 solution); the sample is incubated for six hours at 30° C., and the reaction is finally stopped by the addition of 0.2 ml of 4 N $H_2SO_4$.

The active $CO_2$ evolved during the substratum cleavage is collected in ethanolamine (0.2 ml) and measured in the scintillation counter (0.1 ml samples, each in 15 ml scintillary fluid Zinsser Unisolv I.)

The selectivity factor b is the dimensionless ratio of the radioactivity thus measured:

$$b = \frac{^{14}CO_2 \text{ from side chain of } (26\text{-}^{14}C) - \text{sterol compound}}{^{14}CO_2 \text{ from ring system of } (4\text{-}^{14}C) - \text{sterol compound}}$$

In this equation, sterol compound means the respective radioactively tagged sterol compound used, e.g. corresponding cholesterol or β-sitosterol compounds.

The technique of the determination of the microbiological degradation of sterol compounds by radioactive tagging, either of a ring carbon atom or of a side chain carbon atom, is, in general, a method known in prior art, whose details will be referred to here. Reference is made, for example, to the following publications: Steroids, 677–688 (1964), G. E. Peterson and J. R. Davis "Cholesterol Utilization by Streptomyces spp." and J.B.C. 206, 511–523 (1954) Thressa C. Stadtman et al. "Studies on Microbiological Degradation of Cholesterol".

For the selection of the wild strains in this stage 1 of the process according to the invention, it is furthermore preferable that the selectivity factor b of the wild strains be at least 1, preferably at least 2. The growth factor a of the wild strains should be at least 0.1, preferably at least 0.2 and most preferably at least 1.

When selecting the wild strains best suited for the further stages of the process according to the invention, it may be desirable to balance the factors a and b against each other. Thus, it may be useful in the framework of the invention, to give preference to wild strains having a particularly high selectivity factor b, and when making the choice between different isolated wild strains, to select initially according to the selectivity factor b, with as high a numerical value as is possible for b. Conversely, a particularly good growth—expressed by a very high value for the growth factor—may, of course, be a reason to give preference to such a wild strain for the subsequent mutation followed by the selection of the mutant population.

Such strains as achromobacter, arthrobacter, bacillus, brevibacterium, corynebacterium, flavobacterium, microbacterium, mycobacterium, nocardia, protaminobacterium, serrata or streptomyces may be used as the wild strains in stage 1. The belonging of the particular strain to generic characters is not so much decisive for the process according to the invention. What is important, are rather its previously discussed characteristics during the cultivation on culture media containing sterol compounds and, in particular, its selectivity index I, which is determined by the growth factor a and the selectivity factor b.

Stage 2

The mutation of the wild strain selected is effected in a manner known per se. It may, for example, be achieved by high-energy irradiation with ultraviolet rays or x-rays. However, the treatment with mutagenic agents is also particularly suitable. Suitable mutagenic agents are, for example, nitrosoguanidine compounds such as 1-methyl-3-nitro-1-nitrosoguanidine or ethylmethane sulfonate. In detail, reference can be made in this respect to the general disclosure of the status of the art, see for example U.S. Pat. No. 4,029,549, column 2, lines 57 et seqq., with the references contained therein. Basically, it is also true of the invention that the result of the mutation of the wild strain in uncertain insofar as the characteristics of the defect mutants obtained are not predictable in detail. Nevertheless, principles for optimum initiation of mutation can be established because the laws of statistics are applicable to a population of microorganisms. Methods permitting determination of optimum conditions for the induction of mutations are known from literature (see E. A. Adelberg, M. Mandel, GCC Chen (1965) "Optimal Conditions for Mutagenisis by N-methyl-N'-nitro-N-nitrosoguanidine in Escherichia coli" Biochem. Biophys. Res. Commun. 18, 788–795).

In general, to increase the frequency of mutations in microorganism populations, the concentration and the time of action of the mutagenic agents will be chosen such that already part of the microorganism population is lethally damaged. In this way, the frequency of various mutations increases to a more or less extent in the surviving portion of the population.

Within the process according to the invention, the conditions of concentration and time of action of the mutagenic agent are chosen such that 10–99.999% of the initial population are deactivated by the treatment. Preferably, a killing rate of 90 to 99.99% is chosen. The process stage 2 of mutation is followed by the process stages 3 and 4 which are repeated selection steps for the isolation and accumulation of the desired defect block mutants.

Stage 3

For the succeeding selection of the specific mutants, desired according to the invention out of the large population of the micro-organisms after the mutation treatment, culture conditions according to the invention are chosen, under which the altered specific characteristics of the mutant strains produced become the advantage in the selection. The accumulation of the desired defect mutants is effected according to the invention often under conditions such that the specific mutant does not grow or substantially does not grow, while undesirable accompanying organisms grow and are killed off by or during their growth. In this manner, those block mutant strains are successfully isolated whose ring-degrading enzymes are blocked, but which now as before are capable of degrading the 17-C side chain on the sterol compound, it being ensured by further measures, especially in this stage 3, that just such block mutants can be isolated which form preferentially the alpha- propionic acid group in 17-C position during side chain degradation.

For this purpose, the mutant population is cultivated in process stage 3 on a separation medium which finally serves as the enrichment medium for the desired mutant strains. An aqueous nutrient medium may be used as mutant separation medium, which contains as carbon source a steroid compound with a 17-C side chain with only a limited number of carbon atoms or also no side chain in the 17-C position. Besides the steroid compounds which are not substituted in 17-C position, those which contain side chains with up to five carbon atoms are suitable as carbon source in this mutant separation medium.

It is preferable, however, to use a steroid compound with three carbon atoms in the 17-C side chain as carbon source in this mutant separation or enrichment medium, it being desirable to use a 17-C-steroid-alpha-propionic acid compound or a plurality of such desired 17-C-steroid-alpha-propionic acid compounds as the sole carbon source.

It may be further preferred to use as carbon source in this mutant separation medium those 17-C-steroid-alpha-propionic acid compounds the production of which is ultimately desired by means of the block mutants cultivated according to the invention. Thus, if Δ4 BNC or Δ1,4 BNC is finally to be recovered as the process product from sterols of vegetable or animal origin according to the invention, it may be desirable to use Δ4 BNC and/or Δ1,4 BNC at the sole carbon source in the mutant separation or enrichment medium of this stage 3.

In other respects, the process is operated with conventional nurient solutions under aerobic conditions.

The mutated micro-organisms which, due to the mutation treatment, have lost their ability to grow on the carbon sources now available, are not able to reproduce themselves when the mutant separation medium is incubated, i.e. they do not grow. Another portion of the mutant population which either has not been damaged sufficiently in the mutation treatment of stage 2 or has suffered other defects is capable of growing on the carbon source of the mutant separation medium, i.e. reproduction occurs during incubation.

The invention makes use of this differing behaviour in choosing the conditions in the mutant separation medium so that the growing strains are killed off because of or during their growth while the non-growing mutant strains are not damaged.

Such a separation is possible, for example, by the addition of antibiotics, e.g. by the addition of penicillin compounds. The addition of penicillin compounds leads to the killing-off of the fraction of the growing strains of microorganisms while the non-growing strains remain unharmed.

Another possibility of separating the mutants in this stage is to incorporate cell-damaging, especially radioactive components in the proportion of the mutant population which grows on the separation medium. For example, incorporation of $P^{32}$ in the growing mutant strains is suitable. This may, for example, be effected by the concomitant use of appropriately radioactively labelled salts in the nutrient solution of this selection step. For the separation by means of $P^{32}$, the concomitant use of $NaH_2\,^{32}PO_4$ in the nutrient solution has been found to be useful.

The block mutant aimed at according to the invention may then be isolated from the remaining undamaged block mutants by means of the known Lederberg stamp method. As regards the procedure used here, the penicillin enrichment method, and the Lederberg stamp method, reference is made, for example, to J. Amer. Chem. Soc. 70, 4267, (1948) Davis, B. D. (Penicillin enrichment method), J. Bact. 63, 399 (1952) Lederberg, J. Lederberg, E. M. (Lederberg stamp method).

Stage 4

The defective block mutants thus isolated and selected may now be cultivated on a common culture medium and then, if desired, subjected to a further selection. This selection may be effected, for example, according to the result desired for the microorganism strains on the intended starting material, for example, on natural or vegetable sterol compounds, in which case particularly the chemical nature of the products of metabolism of the growth of the micro-organisms and the growth enthusiasm of the strains may be decisive. Naturally, block mutants, having optimum productivity of the ultimately desired process product will be preferred. These strains may then be used in the commercial-scale process. Cultivation and selection may be repeated here once or several times.

Within the framework of the process according to the invention, it is possible to repeat once or several times the sequence of the process stages, i.e. the mutation according to stage 2 and the succeeding mutant separation according to stage 3, if a stll stronger effect of the mutagenic agents appears desirable on the defective mutant strains for achieving ultimately optimal production results. Finally, processing is then effected generally according to stage 4.

To determine the particularly active defect block mutants desired, a standard test for determining the yield may be used, this test being carried out in the absence of inhibitors under the following test conditions:

The defective block mutant strain to be tested is cultivated in a 500 ml Erlenmeyer flask with 100 ml of nutrient solution having the following composition: 0.8% of peptone, 0.9% of yeast extract, 0.3% of glucose, 0.06% of Tween 80 (polyoxyethylene sorbitane monooleate), 0.06% of cholesterol or sitosterol, pH 7.2. The strain is precultivated on the shaking machine (shaking frequency 150 cpm) at 30° C. for 62 hours. After having added 0.1% of BRIJ 35 (polyoxyethylene monolauryl ether) and 0.1% of the sterol compound, incubation is continued for 120 hours. After having terminated the incubation, samples are taken, extracted and analyzed by thin layer chromatography.

The defective block mutants preferred in accordance with the invention give a yield of 17-C-alpha-propionic acid derivative, especially of Δ-4 BNC and/or Δ-1,4 BNC, of at least 15% by weight and preferably of at least 30% by weight on cholesterol or on sitosterol. On cholesterol, the yield is especially at least 50% by weight and may, for example, range between 70 and 80% by weight, based in each case on sterol charged. On sitosterol, the yields are generally somewhat lower but may, here again, reach, for example, 40 to 50% by weight. Thus, results which were unknown heretofore are achieved for the mode of operation without inhibitors.

Process for the production of
17-C-steroid-alpha-propionic acid compounds and, in particular for the production of
3-oxo-pregna-4-ene-20-carboxylic acid and/or
3-oxo-pregna-1,4-diene-20-carboxylic acid The selective transformation of the steroid substrate selected as starting material, i.e. for example of a natural sterol compound may be effected in a manner known per se after having provided and selected the defective mutants according to the previously described procedure. Thus, for example, the steroid compound selected as starting material may be added to the culture during the incubation period or it may be introduced into the culture medium before the inoculation of the block mutants. One steroid compound or a mixture of a plurality of steroid compounds may be used. The steroid compounds to be selectively degraded are preferably used in the culture in amounts of about 0.1 to 100 g/l. The optimum concentration of the sterol compound to be transformed in the cultivation stage is generally dependent on the strain and may be determined in each case by simple preliminary tests. In general, the concentration of the sterol compound in the medium preferably does not exceed 20 g/liter and, in many cases, 15 g/liter, but amounts of more than 1 g/liter are preferred.

It may be preferred not to add at one time to the reaction the substrate to be subjected to side chain degradation, but to by and by make this addition in the course of the reaction. Preferably, the starting substrate of this embodiment is added substantially continuously in the reaction mixture in the course of the degradation reaction. By this means, the yield of the desired degradation products can be increased.

The culture is cultivated in a growth medium which, as carbon source, contains either the sterols to be transformed or also additional metabolizable carbon sources as well as the nutritive and growth materials usually needed by these microorganisms. Particularly favorable for the growth of the organisms are for example paraffin, glycerol, carboxylic acids, starch, dextrin, saccharose, sucrose, glucose fructose and sugar-containing waste materials. Suitable nitrogen sources include ammonium salts, nitrates, peptone, corn steep liquor, soya metal, distiller's wash and fish meal. Moreover, fermentation accelerators such as yeast extract and vitamins may be added. The nutrient medium additionally contains advantageously inorganic salts such as sodium potassium or ammonium phosphates as well as calcium, magnesium, manganese or iron salts.

The emulsification of the sterols in the culture medium is preferably effected by means of known emulsifiers, e.g. by means of fatty acid, sorbitane esters or their ethylene oxide addition products, polyoxyethylene monolauryl ether or fatty acid amino-alkylbetain.

The culture medium used is preferably sterilized by heating before the beginning of the cultivation of the bacteria. After cooling and inoculation with a suitable seed culture of the transforming bacteria strain, the culture medium is incubated between 25° and 55°, preferably at 27°-30° C. The pH of the culture medium ranges between 4 and 8.5, preferably in the range of 7.0-8.0. The culture is supplied with oxygen by shaking, stirring or injection of gas, and incubated until the sterol is degraded to the desired degree. As a rule, the degradation of the sterol requires from 24 to 160 hours depending on the concentration of the substrate and on the fermentation conditions.

The process product obtained this way and usually accumulated in the fermentation broth may then be recovered from the reaction mixture in a manner known per se. Thus, for example, BNC compounds may be isolated from the culture medium, before or after the separation of the cells, by extraction within organic solvents such as methylisobutylketone, acetic acid ester, n-hexanol, n-octanol, chloroform or n-hexane.

For inst. an isolation of BNC compounds is achieved by extracting one liter of a fermentation broth containing 1 g BNC with about the same volumes of organic solvents such as methylisobutylketone, acetic acid ester, n-hexanol, n-octanol, chloroform, or n-hexane in the perforator, homogenzier, or separating funnel. In the latter two cases, a centrifugation step must be added for the separation of the BNC-containing organic phase from the emulsion.

After evaporating the solvent, a BNC-containing residue is left which after recrystallization, e.g. from benzene, may be processed to pure BNC having a melting point of 233°-236° C.

The solvent extraction is possible, above all, in the acidic pH range. To this end, for example, the sample is adjusted to about pH 2 with 50% $H_2SO_4$ and extracted with methylisobutylketone, acetic acid ester, n-hexanol, n-octanol, chloroform, or n-hexane in the manner described above. After evaporation of the organic phase, a residue containing BNC is also obtained, which again after recrystallization, leads to a pure product having a melting point of 233°-236° C. The extraction may also be performed in the neutral range.

Alternatively, a purification by anion exchange is also possible. To this end, the fermentation broth is first desirably concentrated and the adjusted to an alkaline pH, e.g. 12. After adding a limited amount of methanol and agitating in the homogenizer, the cell mass is separated by means of a basket centrifuge. The supernatant alcohol-water is pumped over a ion-exchange column which is filled with an anion exchanger resin, e.g. in acetate form. The BNC formed is thereby completely bound to the ion-exchanger. Elution with 10 acetic acid in methanol gives a product which chiefly contains BNC. After recrystallization, pure BNC with a melting point of 233°-236° is obtained.

According to a preferred embodiment, the isolation of BNC-compounds from the fermentation liquid is simply realised by precipitation in the acidic range and filtration. To this end, the fermentation liquid adjusted to be alkaline is first filtrated to permit the removal of cell material and of other solid components. Thereafter, one acidifies, and the BNC precipitates in a solid form which can be filtered and may be recovered for inst. by simple filtration under suction.

For the acidification, any mineral acid may be used, but also organic acids, e.g. acetic acid, and even gaseous $CO_2$. With the pH 5, the complete precipitation is practically achieved. It may be favorable for a better filtration possible, to shortly heat the suspension. The isolated solid may contain up to 90% of BNC-compounds. The pure compounds may be recovered by recrystallization. The BNC compounds may be converted to useful steroids such as androstanedione (AD) or androsdienane (ADD) through modified technology as disclosed in U.S. Pat. No. 3,202,683, issued Aug. 24, 1965 to Krieger, et al.

SPECIFIC DETAILS OF THE INVENTION

The teaching of the invention is realizable not only with natural steroid substrates such as cholesterol, sitosterol, etc. Suitable starting materials for the transformation to, for example, Δ-4 and/or Δ-1,4 BNC include derivatives thereof such as cholestenone, sitostenone, stigmastenone and the like. During the course of the development work, it has been found that a wild strain belonging to the group of coryneform bacteria, may be particularly suitable starting material for the recovery of the defect block mutants desired. This strain, Chol. 73 (cultivated from soil samples obtained on the grounds of the Biotechnical Center of Henkel KGaA at Düsseldorf-Holthausen) which has been deposited under the accession number CBS 660.77 in Baarn, the Netherlands, and under the accession number ATCC 31384 in Rockville, Md., USA was examined more closely with respect to morphology and growth physiology. The following characteristics were found:

| | |
|---|---|
| 1. Cell form: | irregular, predominantly short rods, partly coccoid or also longer rods, partially branched, partly angular; very young cultures: with predominantly long, weakly branched rods. |
| 2. Spore formation | negative |
| 3. Gram coloring | positive |
| 4. Colony form on bouillon agar plates | small, round, cream-colored colonies, smooth rim, convex, smooth, shiny |
| 5. Growth on glucose-agar: | growth somewhat more abundant, otherwise as under 4 |
| 6. Growth on glucose-nitrate-agar: | growth somewhat more abundant, otherwise as under 4. |
| 7. Growth on potato agar | colonies in combination somewhat reddish, otherwise as under 4. |
| 8. Growth on glucose-asparagine agar | colonies very much smaller, round cream-colored, smooth rim, shiny. |
| 9. Growth on starch-agar | medium large, round colonies, |

|  |  |  |
|---|---|---|
|  |  | partially lobed, cream-colored, shiny, moister than on BA. |
| 10. | Growth on calcium caseinate agar: | slow growth, no caseolytic ring formation |
| 11. | Growth on skimmed milk: | negative and no coagulation |
| 12. | Indol formation from tryptophane | negative |
| 13. | Acid formation/methyl red test | negative |
| 14. | Voges-Proskauer reaction (acetone formation) | negative |
| 15. | Growth on citrate | very poor to negative |
| 16. | Reduction of $NO_3$ to $NO_2$ | negative |
| 17. | Reduction of $NO_2$ | weakly positive |
| 18. | Carbohydrate utilization | growth on glucose, fructose, sucrose, maltose, mannose, lactose, galactose, mannitol, rhamnose, arabinose, and starch; but in no case gas or acid formation |
| 19. | NaCl-broth | good growth to 3% NaCl, moderate growth to 5%, no growth from 7% |
| 20. | Urea cleavage | positive |
| 21. | Oxygen requirement | strictly aerobic |
| 22. | Growth temperature | growth between 19° and 37° C., good growth around 30° C. |
| 23. | Growth on<br>0.5 g $NaH_2PO_4$<br>1.8 g $K_2HPO_4$<br>0.5 g $MgSO_4 \times 7H_2O$<br>0.2 g $MnSO_4 \times 4H_2O$<br>0.2 g $CaCl_2 \times 2H_2O$<br>0.02 g $FeSO_4 \times 7H_2O$<br>0.5 g $NH_4NO_3$<br>1.0 g Tween 80<br>2.0 g Cholesterol<br>1000 ml distilled $H_2O$,<br>pH 6.8. | small white colonies after 6 days |

This wild strain is mutated by treatment with 1-methyl-3-nitro-1-nitrosoguanidine as described in the following examples. The mutant population is processed by the process according to the invention. This resulted in the recovery of the new block mutant Chol.spec. 73-Mll which is deposited in Baarn, the Netherlands, under accession number CBS 437.77 as well as in Rockville, Md., USA, under accession number ATCC 31385. This new block mutant is suitable for the inhibitor-free production of 3-oxo-pregna-4-ene-20-carboxylic acid/or 3-oxo-pregna-1,4-diene-20-carboxylic acid also in the absence of the inhibitors which inhibit the steroid ring degradation and/or the growth. Thus, for example Δ4 BNC and/or Δ1,4 BNC are recovered in high yields from cholesterol as starting material while only small amounts of AD and/or ADD. were obtained.

A. Recovery of Suitable Wild Strains

According to the customary enrichment methods, sterol-degrading microorganisms were isolated from soil samples which first, in an agar plate test, were tested as to their capability of growing on cholesterol. Strains showing a clear colony growth with cholesterol as the sole C-source are subjected to further selection procedures.

B. Determination of Growth Factor a

To determine the growth factor a, the isolated pure cultures are cultivated aerobically in shaking cultures in the following medium (per liter):

1.0 g $KH_2PO_4$
0.5 g $MgSO_4.7H_2O$
0.1 g NaCl
0.1 g $CaCl_2.2H_2O$
5.0 g $(NH_4)_2SO_4$
1.0 g Tween 80 (polyoxyethylene sorbitane monooleate)
2.0 g 17-C-side chain sterol compound, e.g. cholesterol
0.5 g yeast extract
0.01 g 1-histidine
0.02 g dl-methionine
0.02 g dl-tryptophane
2 μg biotine
400, μg calcium pantothenate
2 μg folic acid
2000 μg inosite
400 μg niacine
200 μg p-aminobenzoic acid
400 μg pyridoxine hydrochloride
200 μg riboflavin
400 μg thiamine hydrochloride
trace element solution
pH of the nutrient medium, 6,8.

To determine optical density of the cell suspension, respective samples are taken in 24 hour intervals, and the extinction (E') is measured in the Zeiss-photometer (type PL 4) at a wave length of 620 nm (d=1 cm) against distilled water. The growth factor a results as maximum optical density at the end of the logarithmic growth phase minus initial extinction $E_o$.

C. Determination of Selection Factor b

The wild strains showing the best growth in the shaking flask with cholesterol are subsequently tested in the Warburg test with 26-$^{14}$C- and 4-$^{14}$C-marked cholesterol as to their capability of degrading the side chains of cholesterol.

The cultivation of strains is performed in a 500 ml Erlenmeyer flask by means of 150 ml of nutrient solution of the following composition: 1.56% of peptone, 0.28% yeast extract, 0.56% NaCl, 0.10% glucose, 0.10% Tween 80, 0.05% cholesterol, pH 7,2. The strains are cultivated for 48 hours at 30° C. on the mechanical shaker, the cells are subsequently removed by centrifugation, washed 2 times in 0.05 m $PO_4$-buffer (pH 7.2) and resuspended in the same volume of buffer.

For the Warburg test, 2,4 ml of cell suspension are incubated with 0,2 ml of cholesterol solution (5μ moles of cholesterol and 20000 cpm 4-$^{14}$C or 26-$C^{14}$). The separated, radioactive $CO_2$ is caught in 0.2 ml ethanolamine (in the central vessel). The reaction is stopped after 6 hours at 30° C. by adding 0.2 ml of 6 N $H_2SO_4$, and at the same time, the amount of $CO_2$ still present in the suspension is expelled. To measure the absorbed $^{14}CO_2$, 0,1 ml of ethanolamine are removed from the Warburg vessel to measure the activity in the szintillation counter (Berthold and Frieseke, type bF 5 000). The selectivity factor b is the quotient of 26-$^{14}CO_2$/4-$^{14}CO_2$.

As stated above, the wild strain Chol 73 was selected, after all, which had a growth factor a=3.71 and a selectivity factor b=5.0. Said strain was used to recover the desired block mutant.

A series of wild strains is listed now hereunder which had a favorable selectivity factor b (26-$^{14}CO_2$/4-$^{14}CO_2$) in the Warburg test:

| Internal Name | Accession No. | Selection Factor b |
| --- | --- | --- |
| SC-18 | DSM 1 419 | 1,1 |
| Sc-89 | DSM 1 421 | 1,2 |
| SC-104 | ATCC 31 455 | 1,9 |
| SC-338 | DSM 1 425 | 1,7 |
| SC-358 | DSM 1 427 | 1,2 |
| SC-372 | DSM 1 428 | 2,3 |

EXAMPLE 2

A. Mutation

Starting from strain Chol 73, mutant Chol 73-mll was isolated in accordance with the mutation- and selection method fully dealt with.

B. Recovery of Mutants with Increased BNC-Yields

1. Mutation Treatment by Means of UV-Radiation

To increase BNC-yields, the mutant strain Chol 73-Mll is subjected to another mutation treatment. The strain is propagated in the following nutrient solution at 30° C. on the mechanical shaker (nutrient solution A): 0.8% peptone, 0.9% yeast extract, 0.3% glucose, 0.06% Tween 80, 0.06% cholesterol, pH 7.2.

Upon reaching the logarithmic growth phase, the cells are removed by centrifuging, washed 2 times with sterile 0,1 m $PO_4$-buffer (pH 6,5), resuspended in the same buffer and under the microscope, the cell density is adjusted to $10^8$ cells/ml. 8 ml of said cell suspension are passed into a petri dish and radiated for 90 sec. under the uv-lamp (distance 30 m, uv-radiation lamp of E. Schütt jun., Göttingen).

C. Selection and Isolation of Desired Mutant Strains

1. Enrichment of Strains having Reduced Final Product Inhibition

The uv-radiated cell suspension is subsequently cultivated in the following nutrient solution: 0.05% $NaH_2PO_4$, 0.20% $K_2HPO_4$, 0.05% $MgSO_4.7H_2O$, 0.02% $CaCl_2.2H_2O$, 0.005% $MnSO_4.4H_2O$, 0.005% $(Fe)_2SO_4.7H_2O$, 0.10% $(NH_4)_2SO_4$, 0.001% Biotine, 0.10% BRIJ 35, ( polyoxyethylene monolauryl ether), 0.50% cholesterol, 0.50% BNC, pH 7,2. After an incubation time of 72 hours at 30° C., one ml of the culture solution is passed into fresh nitrient solution A to be cultivated again aerobically for 48 hours at 30° C.

2. Penicillin Method

To eliminate possible revertants, the grown culture solution is subsequently subjected to a penicillin treatment. 0,1 ml of the cell suspension are passed into 10 ml of the following nutrient solution: 0.05% $NaH_2PO_4$, 0.20% $K_2HPO_4$, 0.05% $MgSO_4.7H_2O$, 0.02% $CaCl_2.2H_2O$, 0.005% $MnSO_4.4H_2O$, 0.005%$(Fe)_2SO_4.7H_2O$, 0.10% $(NH_4)_2SO_4$, 0.001% biotine, 0.10% BRIJ 35 (polyoxyethylene monolauryl ether), 0.10% BNC, pH 7,2. After a shaking time of 18 hours at 30° C. a dilution is made with fresh, prewarmed nutrient solution of the same composition to about $10^6$ cells per ml. 1000 IU penicillin G are added and incubation for further 5 hours at 30° C. is carried out. The antibioticum will be then removed by centrifuging of the cells and washing with sterile, physiologic sodium chloride solution, and the cells are incubated in the above medium with 1,0% cholesterol in place of BNC, for further 48 hours. Then, the cell suspension is plated on the same nutrient medium plus 1,6% agar and the colonies showing on the same medium with increased substrate concentration the best growth are used as strain cultures.

By this means, strains were isolated which, upon incubation with cholesterol, gave good yields of BNC. The following strains were deposited in the German Collection for Microorganisms (DSM) in Göttingen:

| Internal Name | Accession No. | BNC Yields |
| --- | --- | --- |
| T 137 | DSM 1 425 | 315 mg/100 ml |
| T 139 | DSM 1 437 | 305 mg/100 ml |
| T 162 | DSM 1 439 | 321 mg/100 ml |
| T 166 | DSM 1 442 | 308 mg/100 ml |
| T 190 | DSM 1 443 | 318 mg/100 ml |
| T 191 | DSM 1 444 | 392 mg/100 ml |
| T 244 | DSM 1 445 | 302 mg/100 ml |

EXAMPLE 3

A. BNC Yields of the Most Active Mutant Strains

The strains are cultivated aerobically in 500 ml Erlenmeyer flask with 100 ml nutrient solution of the following composition: 0.5% peptone, 0.8% yeast extract, 0.4% corn gluten, 0.3% glucose, 0.05% Tween 80. 0,05% cholesterol, pH 7.2. The culture was precultivated on the mechanical shaker (shaking frequency 150 rpm) at 30° C. for 48 hours, then, 0.2% of emulsifier and 0.5% of cholesterol are added and incubation for further 120 hours is performed. Upon termination of the cultures samples were taken, adjusted to pH 2.0, extracted with ethyl acetate 1:1, and analyzed by thin layer chromatography. The yields of the individual strains are listed in Example 2 in the Table under C/2.

EXAMPLE 4

The accumulation of undesired metabolite cholest-4-ene-3-on and cholesta-1,4-diene-3-on from the substrate cholesterol by the strain ATCC 31 385 may be substantially suppressed when the substrate to be transformed is continuously added to the reaction mixture. This is applicable correspondingly to the other sterol substrates.

Two 1 l-fermenter with 400 ml sterile nutrient solution (0.9% peptone, 0.9% corn swelling water, 0.9% yeast extract, 0.5% $K_2HPO_4$, 0.5% glycerol, 0.1% polypropylene glycol, pH 6,5) are inoculated with 50 ml of a well grown preculture of the strain ATCC 3 185, which had been incubated in a nutritive medium (0.9% pepton, 0.9% yeast extract, 0.5% glycerol, pH 6.5) for 48 hours at 30° C. The fermenters are agitated at 30° C. and ventilated with 500 ml air/min.

After 24 hours of incubation, an emulsion of 5 g of cholesterol, 1 g of sorbitane monostearate, 4 ml of polypropylene glycol and 4 ml 1 N NaOH in 100 ml of $H_2O$ are fed into the fermenter by a dosing pump. The dosing pump delivers 5 ml suspension per hour, so that the addition of substrate took place from the 24th hour of fermentation to the 44th hour of fermentation. After 44 and 78 hours, 100 ml culture broth were taken from the fermenter, upon acidifying with sulfuric acid and extraction with methylisobutylketone, the fermentation products were determined quantitatively by means of thin layer chromatography.

In the control batch the total amount of substrate was fed to the fermenter after 24 hours.

With a continuous addition of the substrate, the following amounts were determined after 44 hours of fermentation: (mg/100 ml): cholesterol 120, cholestenone plus cholestadienone 40, bisnorcholenone acid 100; after 78 hours of fermentation: cholesterol 20, cholestenone plus cholestadienone 5, bisnorcholenone acid 260.

With a batchwise addition of the substrate, the following determination was made after 44 hours of fermentation (mg/100 ml): cholesterol 100, cholestenone plus cholestadienone 240, bisnorcholenone acid 80; after 78 hours of fermentation: cholesterol 40, cholestenone 100, bisnorcholenone acid 180.

EXAMPLE 5

Mutation Treatment with Methane Sulfonic Acid Ethyl Ester.

Strain SC 104 is cultivated in a nutrient solution of 0.9% peptone plus 0.8% yeast extract and removed by centrifugation upon reaching the logarithmic growth phase, washed two times with sterile phosphate buffer (0.5 M, pH 7.5) and resuspended in the same buffer so that cell density is $10^8$ cells/ml. Methane sulfonic acid ethyl ester is added to the cell suspension so that concentration of the mutageneous substance is 0.1 M. The batch is shaken for 2 hours at room temperature, then, the cells are removed by centrifugation, washed twice with phosphate buffer and finally resuspended in fresh nutritive solution and incubated.

EXAMPLE 6

Recovery of the mutant CBS 437.77 or ATCC 31385 from the wild strain Chol. 73 (CBS 660.77 or ATCC 31384).

(A) A great number of sterol-degrading micro-organisms was isolated from soil samples according to the usual enrichment methods.

Among the strains, microorganisms which degrade sterols preferentially from the side chain were sought thereafter by incubation with cholesterol tagged by 4–14 C and 26–14 C.

The strain Chol 73 showed the highest degradation rates with 26–14 C-cholesterol and thus appeared to be particularly suitable for the selection of degradation defective mutants.

The method of mutant isolation described below is applicable not only to the strain under consideration, Chol 73, which belongs to the group of the coryneform bacteria, but also to any other species.

The mutation of the strain Chol. 73 was effected by treatment with 1-methyl-3-nitro-1-nitrosoguanidine. The cells were cultivated in medium A at 30° for 48 hours.

Medium A:
1.0% yeast extract
1.0% peptone
0.5% glucose
pH 7.5

The cell culture with a cell titer of $2 \times 10^8$ cells/ml was treated for one hour at 30° C. with the mutagenic compound (1 mg/ml) and cultivated three further days in culture medium B to a cell titer greater than $10^9$ cells/ml.

Medium B:
0.05% sodium dihydrogen phosphate
0.20% dipotassium hydrogen phosphate
0.05% magnesium sulfate . 7 $H_2O$
0.02% calcium chloride . 2 $H_2O$
0.005% manganese sulfate . 4 $H_2O$
0.005% iron-II-sulfate . 7 $H_2O$
0.10% ammonium sulfate
0.0001% D-biotine.

(B) One tenth (0.1) ml of the culture solution thus obtained was introduced into 10 ml of culture medium B with the addition of 0.1% polyoxymethylene monolauryl ether and 0.1% 3-oxo-pregna-1,4-diene-20-carboxylic acid and incubated for 36 hours at 30° C. To promote the mutants with defects in the ring degradation system, the mixture was diluted with fresh, prewarmed growth medium of the same composition to $10^6$ cells/ml; 1000 I.U. penicillin G was added per ml, and the new mixture was incubated for further 24 hours at 30° C. then, the cells were washed and distributed on agar plates with growth medium B plus 2% agar and 0.5% glycerol. After reproduction of the cells, to form colonies of visible size, they were transferred by the replica plating technique to nutritive agar B plus 0.1% polyoxyethylene monolauryl ether and 0.1% 3-oxo-pregna-1,4-diene-20-carboxylic acid and again incubated. In the framework of this screening, more than 50 mutant colonies were isolated which did not grow any longer on the steroid-containing nutrient plate after replica plating.

For the selection of the most interesting mutants, the strains were inoculated into 2 ml of nutrient solution A, incubated for 24 hrs. at 30° C., and, thereafter, mixed with 0.2% polyoxyethylene monolauryl ether and 0.2% cholesterol; after further 72 hrs., the culture solutions were analyzed. The contents of the tubes were each shaken with 0.5 ml metylisobutylketone and centrifuged; aliquote amounts of the organic phase were applied to Merck silica gel plates and developed in benzene-ethyl acetate (70+30) developer. The detection of the steroids on the chromatography plates was performed by spraying with a mixture (1+1) of concentrated $H_2SO_4$ and ethanol and then by heating to 120° C. By this means, the strain CBS 437.77 or ATCC 31385 was recognized as a mutant which possesses a block in the degradation of the sterol ring system.

EXAMPLE 7

For a close testing of the sterol transformation by corynebacterium CBS 437.77 or ATCC 31385, the strain was precultivated in a shaking flask with 100 ml of nutrient solution A for 24 hours at 30° C. at a shaking rate of 150 cpm. Thereafter, 0.1% polyoxyethylene sorbitane monooleate and 0.1% cholesterol solution were added and samples were taken and analyzed at various times.

Twenty (20) ml of the culture solution were adjusted to pH 2.0 with 2 N sulfuric acid and extracted in the perforator for three hours with methylisobutylketone, acetic acid ester, n-hexanol, n-octanol, chloroform, or n-hexane. Aliquot amounts of the organic phase were spread on Merck silica gel plates and developed in toluene-butanol (80+20) developer. The evaluation of the chromatography was effected with a thin layer scanner at 250 nm. As the main component of the cholesterol transformation, there were found 50 mg of 3-oxo-pregna-1,4-diene-20-carboxylic acid in addition to small amounts of androst-4-ene-3,17-dione and androst-1,4-diene-3,17-dione.

EXAMPLE 8

For further testing of the sterol transformation by coryne-bacterium spec. CBS 437.77 or ATCC 31385, the strain was precultivated in a shaking flask with 100 ml of nutrient solution A for 24 hours at 30° C. at a shaking rate of 150 cpm. After this, 0.1% polyoxyethylene sorbitane monooleate and 0.01% sitosterol solution were added, and samples were taken and anlyzed at varous times.

Twenty (20) ml of the culture solution was adjusted to pH 2.0 with 2 N sulfuric acid and extracted in the perforator for three hours with ethyl acetate. Aliquot parts of the organic phase were spread on Merck silica gel plates and developed in the toluene-butanol (80–20) developer. The evaluation of the chromatography was effected with a thin layer scanner at 250 nm. This revealed the formation of 20-carboxy-pregna-1,4-diene-3-one and 20-carboxy-pregna-4-ene-3-one in addition to small amounts of androst-4-ene-3,17-dione and androst-1,4-diene-3,17-dione.

EXAMPLE 9

The culture solution of Example 7 was concentrated in the rotation evaporator to ¼ of its starting volume, adjusted with NaOH to pH 13, mixed with three times the volume of methanol and the cell mass was finally removed by centrifugation. The cell-free culture solution was passed via an anion exchanger column in acetate form and by elution with methanol, androst-4-ene-3,17-dione, androst-1,4-diene-3,17-dione and traces of cholestenone were first separated. 20-carboxy-pregna-4-ene-3-on and 20-carboxy-pregna-1,4-diene-3-on were subsequently separated from the ion exchanger with 10% acetic acid and enriched. The enriched eluate was evaporated to dryness, taken up with 5% ammonia while slightly heating, cooled to 4° C. and the precipitated products were removed by filtration. By repeated solubilization, extraction in ether and recrystallization from benzene, the 3-oxo-pregna-1,4-diene-20 carboxylic acid could be substantially purified.

What is claimed is:

1. A process for producing a 17-C-steriod-alpha-propionic acid selected from the group consisting of 3-oxo-pregna-4-ene-20-carboxylic acid, 3-oxo-pregna-1,4-diene-20-carboxylic acid, and mixtures thereof by microbial side chain degradation on 17-C side chain steroid substrates comprising,
   (a) cultivating a defect block mutant microorganism capable of selectively degrading side chains at the C-17 position of a steroid without substantially degrading the steroid rings and not degrading an α-propionic acid residue at said C-17 position in an aqueous culture medium under aerobic conditions in the presence of a steroid substrate until there is an accumulation of said steroid acid, and
   (b) isolating said steroid acid.

2. A process according to claim 1 wherein the block mutants employed are cultivated from wild strains which yield through growth on steroid compounds a selective degradation effect under standard conditions according to the general formula $I = a \cdot 10^b$ wherein a is the growth factor and b is the selectivity factor of the wild strain and the selectivity index I shows a numerical value of at least 10.

3. A process according to claim 2 wherein the selectivity index I of the wild strain is at least $10^5$.

4. A process according to claim 2 wherein the selectivity factor b of the wild strain employed for the cultivation of the blocked mutants is at least 1 and the growth factor a is at least 0.2.

5. A process according to claim 2 wherein the strains growing on the mutants separation medium are eliminated by the additional of antibiotics or with the use of phosphorus 32 and wherein the non-growing defect blocked mutants are present and are not eliminated.

6. A process according to claim 5 wherein the mutant separation medium is an aqueous nutrient medium which contains as the carbon source at least one 17-C-steroid-alpha-propionic acid.

7. A process according to claim 6 wherein 17-C-steroid-alpha-propionic acid compound(s) desired as the end product of the process are used as the sole carbon source in the mutant separation medium.

8. A process according to claim 5 wherein the cultivation of the non-eliminated strain is effected in the absence of an inhibitor selected from the group consisting of alpha, alpha'dipyridyl, 8-hydroxyquinoline and mixtures thereof.

9. A process according to claim 8 wherein the blocked mutant employed is selected from the group consisting of Achromobacter, Arthrobacter, Bacillus, Brevibacterium, Corynebacterium, Flavobacterium, Microbacterium, Mycobacterium, Nocardia, Protaminobacterium, Serratia Streptomyces and mixtures thereof.

10. A process according to claim 9 wherein the steroid compound is selected from the group consisting of cholesterol, sitosterol, stigmasterol, campesterol, ergosterol, cholestenone, sitosteneone, stigmastenone and mixtures thereof.

11. A process according to claim 2 wherein the defective block mutant has been prepared from the wild strains consisting of Chol. spec. 73 (CBS 660.77 or ATCC 31384).

12. A process according to claim 2 wherein the defective block mutant is selected from the group consisting of Chol. spec. 73-M11 (CBS 437.77 or ATCC 31385) and DMS 1 444.

13. A process according to claim 2 wherein the steroid compound having the 17-C side chain contains from 8 to 10 carbon atoms in the side chain and is selected from the group consisting of those steroids having saturated and unsaturated side chains and mixtures thereof.

14. A process according to claim 2 wherein the steroid substrate to be transformed is added to the reaction zone on a substantially continuous basis.

15. A process according to claim 1 wherein the cultivation is performed in the absence of inhibitors which prevent the degradation of the steroid ring.

16. A biologically pure culture of a microorganism having the identifying characteristics of strain CBS 437.77 (ATCC 31385) and the capacity to produce in isolatable amounts a steroid selected from the group consisting of 3-oxo-pregna-4-ene-20-carboxylic acid, 3-oxo-pregna-1,4-diene-20-carboxylic acid and mixtures thereof.

17. A biologically pure culture of a microorganism having the identifying characteristics of a strain selected from the group consisting of strain DSM 1435, strain DSM 1437, strain DSM 1439, strain DSM 1442, strain DSM 1444 and strain DSM 1445 and the capacity to produce in insolatable amounts a steroid selected from the group consisting of 3-oxo-pregna-4-ene-20-carboxylic acid, 3-oxo-pregna-1,4-diene-20-carboxylic acid and mixtures thereof.

* * * * *